US012268391B2

(12) United States Patent
Somekh et al.

(10) Patent No.: US 12,268,391 B2
(45) Date of Patent: *Apr. 8, 2025

(54) ADVANCING A TOOTHED RACK OF A SURGICAL HANDLE ASSEMBLY

(71) Applicant: Lexington Medical, Inc., Bedford, MA (US)

(72) Inventors: Gonen Somekh, Kerem Maharal (IL); Anton Agafonov, Haifa (IL); Andrew Marecki, West Boylston, MA (US)

(73) Assignee: Lexington Medical, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/129,317

(22) Filed: Mar. 31, 2023

(65) Prior Publication Data

US 2023/0233207 A1 Jul. 27, 2023

Related U.S. Application Data

(63) Continuation of application No. 17/113,865, filed on Dec. 7, 2020, now Pat. No. 11,617,583, which is a
(Continued)

(51) Int. Cl.
*A61B 17/072* (2006.01)
*A61B 17/00* (2006.01)
*A61B 17/29* (2006.01)

(52) U.S. Cl.
CPC .......... *A61B 17/07207* (2013.01); *A61B 2017/00367* (2013.01); *A61B 2017/00477* (2013.01);
(Continued)

(58) Field of Classification Search
CPC ............ A61B 17/07207; A61B 17/105; A61B 17/068; A61B 17/1155
See application file for complete search history.

(56) References Cited

U.S. PATENT DOCUMENTS

RE28,932 E    8/1976  Noiles et al.
4,725,764 A   2/1988  Prestel
(Continued)

FOREIGN PATENT DOCUMENTS

CN    1985768      6/2007
CN    101194853    6/2008
(Continued)

OTHER PUBLICATIONS

International Search Report and Written Opinion dated Apr. 7, 2020 for PCT Application No. PCT/US2020/013694 filed Jan. 15, 2020, 8 pages.
(Continued)

*Primary Examiner* — Nathaniel C Chukwurah
(74) *Attorney, Agent, or Firm* — Perkins Coie LLP

(57) ABSTRACT

The present disclosure includes apparatuses for a surgical handle assembly. An example apparatus includes a toothed rack, a movable handle member, a driving pawl configured to engage the toothed rack and advance the toothed rack in a linear distal direction in response to a movable handle member advancing in a proximal direction and a latch configured to engage the toothed rack and advance the toothed rack in a linear proximal direction in response to the movable handle member advancing in a distal direction.

20 Claims, 10 Drawing Sheets

Related U.S. Application Data continuation of application No. 16/249,520, filed on Jan. 16, 2019, now Pat. No. 10,856,871.

(52) U.S. Cl.
CPC ............... *A61B 2017/07271* (2013.01); *A61B 2017/2923* (2013.01); *A61B 2017/2925* (2013.01)

(56) References Cited

U.S. PATENT DOCUMENTS

| | | | |
|---|---|---|---|
| 4,737,608 A | 4/1988 | Jones | |
| 4,978,049 A | 12/1990 | Green | |
| 5,300,081 A | 4/1994 | Young et al. | |
| 5,326,013 A | 7/1994 | Green et al. | |
| RE34,680 E | 8/1994 | Lieser | |
| 5,467,911 A | 11/1995 | Tsuruta et al. | |
| 5,474,223 A | 12/1995 | Viola et al. | |
| 5,484,095 A | 1/1996 | Green et al. | |
| 5,489,058 A | 2/1996 | Plyley et al. | |
| 5,489,292 A | 2/1996 | Tovey et al. | |
| 5,507,426 A | 4/1996 | Young et al. | |
| 5,522,534 A | 6/1996 | Viola et al. | |
| 5,535,935 A | 7/1996 | Mdal et al. | |
| 5,586,711 A | 12/1996 | Plyley et al. | |
| 5,588,579 A | 12/1996 | Schnut et al. | |
| 5,601,224 A | 2/1997 | Bishop et al. | |
| 5,736,703 A | 4/1998 | Kim | |
| 5,758,814 A | 6/1998 | Gallagher et al. | |
| 5,762,256 A | 6/1998 | Mastri et al. | |
| 5,799,857 A | 9/1998 | Robertson et al. | |
| 5,823,066 A | 10/1998 | Huitema et al. | |
| 5,836,503 A | 11/1998 | Ehrenfels et al. | |
| 5,865,361 A | 2/1999 | Milliman et al. | |
| 5,901,895 A | 5/1999 | Heaton et al. | |
| 6,109,500 A | 8/2000 | Alli et al. | |
| 6,281,453 B1 | 8/2001 | Uleski | |
| 6,302,798 B1 | 10/2001 | Nakaguro et al. | |
| 6,905,057 B2 | 6/2005 | Swayze et al. | |
| 6,945,444 B2 | 9/2005 | Gresham et al. | |
| 6,957,758 B2 | 10/2005 | Aranyi | |
| 7,044,352 B2 | 5/2006 | Shelton et al. | |
| 7,044,353 B2 | 5/2006 | Mastri et al. | |
| 7,083,075 B2 | 8/2006 | Swayze et al. | |
| 7,097,089 B2 | 8/2006 | Marczyk | |
| 7,128,254 B2 | 10/2006 | Shelton et al. | |
| 7,143,923 B2 | 12/2006 | Shelton et al. | |
| 7,143,924 B2 | 12/2006 | Scirica et al. | |
| 7,168,604 B2 | 1/2007 | Milliman et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,246,734 B2 | 7/2007 | Shelton | |
| 7,303,106 B2 | 12/2007 | Milliman et al. | |
| 7,325,713 B2 | 2/2008 | Aranyi | |
| 7,364,060 B2 | 4/2008 | Milliman | |
| 7,380,695 B2 | 6/2008 | Doll et al. | |
| 7,380,696 B2 | 6/2008 | Shelton et al. | |
| 7,398,907 B2 | 7/2008 | Racenet et al. | |
| 7,404,508 B2 | 7/2008 | Smith et al. | |
| 7,416,101 B2 | 8/2008 | Shelton et al. | |
| RE40,514 E | 9/2008 | Mastri et al. | |
| 7,422,136 B1 | 9/2008 | Marczyk | |
| 7,455,208 B2 | 11/2008 | Wales et al. | |
| 7,490,749 B2 | 2/2009 | Schall et al. | |
| 7,494,038 B2 | 2/2009 | Milliman | |
| 7,516,877 B2 | 4/2009 | Aranyi | |
| 7,546,940 B2 | 6/2009 | Milliman et al. | |
| 7,611,038 B2 | 11/2009 | Racenet et al. | |
| 7,624,902 B2 | 12/2009 | Marczyk et al. | |
| 7,658,311 B2 | 2/2010 | Boudreaux | |
| 7,694,865 B2 | 4/2010 | Scirica | |
| 7,753,245 B2 | 7/2010 | Boudreaux et al. | |
| 7,780,055 B2 | 8/2010 | Scirica et al. | |
| 7,784,663 B2 | 8/2010 | Shelton | |
| 7,794,475 B2 | 9/2010 | Hess et al. | |
| 7,802,712 B2 | 9/2010 | Milliman et al. | |
| 7,819,296 B2 | 10/2010 | Hueil et al. | |
| 7,824,426 B2 | 11/2010 | Racenet et al. | |
| 7,832,408 B2 | 11/2010 | Shelton, IV et al. | |
| 7,837,079 B2 | 11/2010 | Holsten et al. | |
| 7,845,535 B2 | 12/2010 | Scircia | |
| 7,857,187 B2 | 12/2010 | Milliman | |
| 7,922,063 B2 | 4/2011 | Racenet et al. | |
| 7,926,692 B2 | 4/2011 | Racenet et al. | |
| 7,963,431 B2 | 6/2011 | Scirica | |
| 7,967,178 B2 | 6/2011 | Scirica et al. | |
| 7,967,180 B2 | 6/2011 | Scirica | |
| 8,020,743 B2 | 9/2011 | Shelton | |
| 8,056,789 B1 | 11/2011 | White et al. | |
| 8,061,576 B2 | 11/2011 | Cappola | |
| 8,070,036 B1 | 12/2011 | Knodel | |
| 8,070,836 B2 | 12/2011 | Ng et al. | |
| 8,123,101 B2 | 2/2012 | Racenet et al. | |
| 8,136,712 B2 | 3/2012 | Zingman | |
| 8,141,763 B2 | 3/2012 | Milliman | |
| 8,157,148 B2 | 4/2012 | Scirica | |
| 8,186,555 B2 | 5/2012 | Shelton et al. | |
| 8,210,411 B2 | 7/2012 | Yates et al. | |
| 8,235,274 B2 | 8/2012 | Cappola | |
| 8,292,157 B2 | 10/2012 | Smith et al. | |
| 8,308,040 B2 | 11/2012 | Huang et al. | |
| 8,328,822 B2 | 12/2012 | Huitema et al. | |
| 8,336,751 B2 | 12/2012 | Scirica | |
| 8,336,754 B2 | 12/2012 | Cappola et al. | |
| 8,342,378 B2 | 1/2013 | Marczyk et al. | |
| 8,360,296 B2 | 1/2013 | Zingman | |
| 8,413,468 B2 | 4/2013 | Pigorini | |
| 8,413,868 B2 | 4/2013 | Cappola | |
| 8,414,577 B2 | 4/2013 | Boudreaux et al. | |
| 8,424,736 B2 | 4/2013 | Scirica et al. | |
| 8,499,992 B2 | 8/2013 | Whitman et al. | |
| 8,506,557 B2 | 8/2013 | Zemlok et al. | |
| 8,517,241 B2 | 8/2013 | Nicholas et al. | |
| 8,573,460 B2 | 11/2013 | Cappola | |
| 8,573,463 B2 | 11/2013 | Scirica et al. | |
| 8,574,463 B2 | 11/2013 | Tani et al. | |
| 8,584,919 B2 | 11/2013 | Hueil et al. | |
| 8,608,043 B2 | 12/2013 | Scirica | |
| 8,608,045 B2 | 12/2013 | Smith et al. | |
| 8,622,894 B2 | 1/2014 | Banik et al. | |
| 8,684,247 B2 | 4/2014 | Scirica et al. | |
| 8,684,249 B2 | 4/2014 | Racenet et al. | |
| 8,685,004 B2 | 4/2014 | Zemlock et al. | |
| 8,695,865 B2 | 4/2014 | Smith et al. | |
| 8,708,211 B2 | 4/2014 | Zemlok et al. | |
| 8,708,213 B2 | 4/2014 | Shelton et al. | |
| 8,806,973 B2 | 8/2014 | Ross et al. | |
| 8,820,607 B2 | 9/2014 | Marczyk | |
| 8,888,762 B2 | 11/2014 | Whitman | |
| 8,888,814 B2 | 11/2014 | Cappola | |
| 8,894,647 B2 | 11/2014 | Beardsley et al. | |
| 8,910,847 B2 | 12/2014 | Nalagatla et al. | |
| 8,925,783 B2 | 1/2015 | Zemlok et al. | |
| 9,113,876 B2 | 8/2015 | Racenet et al. | |
| 9,155,529 B2 | 10/2015 | Beardsley et al. | |
| 9,204,876 B2 | 12/2015 | Cappola et al. | |
| 9,232,944 B2 | 1/2016 | Cappola et al. | |
| 9,265,585 B2 | 2/2016 | Wingardner et al. | |
| 9,320,519 B1 | 4/2016 | Knodel | |
| 9,364,218 B2 | 6/2016 | Scirica | |
| 9,364,226 B2 | 6/2016 | Zemlok et al. | |
| 9,393,016 B2 | 7/2016 | Scirica et al. | |
| 9,445,810 B2 * | 9/2016 | Cappola | A61B 17/07207 |
| 9,465,873 B1 | 10/2016 | Franke et al. | |
| 9,474,528 B2 | 10/2016 | Marczyk | |
| 9,498,216 B2 | 11/2016 | Williams | |
| 9,522,029 B2 | 12/2016 | Yates et al. | |
| 9,539,006 B2 | 1/2017 | Collings et al. | |
| 9,554,803 B2 | 1/2017 | Smith et al. | |
| 9,636,091 B2 | 5/2017 | Beardsley et al. | |
| 9,655,617 B2 | 5/2017 | Cappola | |
| 9,668,731 B2 | 6/2017 | Zemlok et al. | |
| 9,668,735 B2 | 6/2017 | Beetel | |

(56) References Cited

U.S. PATENT DOCUMENTS

| | | |
|---|---|---|
| 9,820,738 B2 | 11/2017 | Lytle et al. |
| 9,839,425 B2 | 12/2017 | Zergiebel et al. |
| 9,861,358 B2 | 1/2018 | Marczyk et al. |
| 9,867,675 B2 | 1/2018 | Beardsley et al. |
| 9,872,673 B2 | 1/2018 | Beardsley et al. |
| 9,918,713 B2 | 3/2018 | Zergiebel et al. |
| 9,931,739 B2 | 4/2018 | Nelson et al. |
| 9,968,276 B2 | 5/2018 | Koktzoglou |
| 9,987,029 B2 | 6/2018 | Beardsley et al. |
| 9,993,258 B2 | 6/2018 | Shelton et al. |
| 10,004,504 B2 | 6/2018 | Bryant |
| 10,098,637 B2 | 10/2018 | Zergiebel et al. |
| 10,105,139 B2 | 10/2018 | Yates et al. |
| 10,383,634 B2 | 8/2019 | Shelton, IV |
| 10,433,842 B2 | 10/2019 | Amariglio et al. |
| 10,856,871 B2 * | 12/2020 | Somekh ........... A61B 17/07207 |
| 11,103,247 B2 | 8/2021 | Amariglio et al. |
| 11,166,723 B2 | 11/2021 | Somekh et al. |
| 11,617,583 B2 | 4/2023 | Somekh et al. |
| 11,622,764 B2 | 4/2023 | Marecki et al. |
| 12,089,846 B2 | 9/2024 | Marecki et al. |
| 2001/0030219 A1 | 10/2001 | Green et al. |
| 2004/0232199 A1 | 11/2004 | Shelton et al. |
| 2005/0006429 A1 | 1/2005 | Wales et al. |
| 2005/0116009 A1 | 6/2005 | Milliman |
| 2006/0079912 A1 | 4/2006 | Whitfield et al. |
| 2006/0111210 A1 | 5/2006 | Hinman |
| 2007/0125826 A1 | 6/2007 | Shelton |
| 2007/0262116 A1 | 11/2007 | Hueil et al. |
| 2008/0017693 A1 | 1/2008 | Mastri et al. |
| 2008/0083810 A1 | 4/2008 | Marczyk |
| 2008/0179374 A1 | 7/2008 | Beardsley et al. |
| 2008/0296346 A1 | 12/2008 | Shelton et al. |
| 2008/0314958 A1 * | 12/2008 | Scirica ............. A61B 17/07207 |
| | | 227/179.1 |
| 2009/0062614 A1 | 3/2009 | Adzich et al. |
| 2009/0145947 A1 | 6/2009 | Scirica et al. |
| 2009/0272614 A1 | 11/2009 | Watarai |
| 2010/0001036 A1 | 1/2010 | Marczyk et al. |
| 2010/0264193 A1 | 10/2010 | Huang et al. |
| 2011/0009850 A1 | 1/2011 | Main et al. |
| 2011/0062211 A1 | 3/2011 | Ross et al. |
| 2011/0166585 A1 | 7/2011 | Roth et al. |
| 2011/0253765 A1 | 10/2011 | Nicholas et al. |
| 2011/0290854 A1 | 12/2011 | Timm et al. |
| 2011/0295313 A1 | 12/2011 | Kerr |
| 2012/0080477 A1 | 4/2012 | Leimbach et al. |
| 2012/0116391 A1 | 5/2012 | Houser et al. |
| 2012/0286019 A1 | 11/2012 | Hueil et al. |
| 2012/0293103 A1 | 11/2012 | Forster et al. |
| 2013/0030428 A1 | 1/2013 | Worrell et al. |
| 2013/0053831 A1 | 2/2013 | Johnson et al. |
| 2013/0092719 A1 | 4/2013 | Kostrzewski |
| 2013/0098966 A1 | 4/2013 | Kostrzewski et al. |
| 2013/0168435 A1 | 7/2013 | Huang et al. |
| 2013/0199327 A1 | 8/2013 | Park et al. |
| 2013/0245676 A1 | 9/2013 | Cappola |
| 2013/0304115 A1 | 11/2013 | Miyamoto |
| 2014/0001231 A1 | 1/2014 | Shelton et al. |
| 2014/0224856 A1 | 8/2014 | Smith et al. |
| 2014/0263543 A1 | 9/2014 | Leimbach et al. |
| 2014/0276949 A1 | 9/2014 | Staunton et al. |
| 2015/0053749 A1 | 2/2015 | Shelton et al. |
| 2015/0196966 A1 | 7/2015 | Tsai |
| 2015/0196996 A1 | 7/2015 | Nelson et al. |
| 2015/0209059 A1 | 7/2015 | Trees et al. |
| 2015/0297216 A1 | 10/2015 | Williams |
| 2015/0342605 A1 | 12/2015 | Abbott et al. |
| 2015/0374396 A1 | 12/2015 | Strobl et al. |
| 2016/0058441 A1 | 3/2016 | Morgan et al. |
| 2016/0074106 A1 | 3/2016 | Garrison |
| 2016/0089175 A1 | 3/2016 | Hibner et al. |
| 2016/0166250 A1 | 6/2016 | Marczyk |
| 2016/0270786 A1 | 9/2016 | Scirica |
| 2017/0000485 A1 | 1/2017 | Shelton et al. |
| 2017/0172577 A1 | 6/2017 | Wenchell et al. |
| 2017/0224334 A1 | 8/2017 | Worthington et al. |
| 2017/0224343 A1 | 8/2017 | Baxter et al. |
| 2017/0252096 A1 | 9/2017 | Felder et al. |
| 2017/0281177 A1 | 10/2017 | Harris et al. |
| 2017/0281184 A1 | 10/2017 | Shelton et al. |
| 2017/0281220 A1 | 10/2017 | Hibner et al. |
| 2018/0021041 A1 | 1/2018 | Zhang et al. |
| 2018/0078354 A1 | 3/2018 | Cardinale et al. |
| 2018/0091145 A1 | 3/2018 | Dey et al. |
| 2018/0168599 A1 | 6/2018 | Bakos et al. |
| 2018/0289370 A1 | 10/2018 | Amariglio et al. |
| 2018/0310935 A1 | 11/2018 | Wixey |
| 2018/0317915 A1 | 11/2018 | McDonald |
| 2018/0368832 A1 | 12/2018 | Marecki et al. |
| 2019/0183491 A1 | 6/2019 | Shelton et al. |
| 2019/0261984 A1 | 8/2019 | Nelson et al. |
| 2019/0290265 A1 | 9/2019 | Shelton et al. |
| 2020/0008801 A1 | 1/2020 | Somekh et al. |
| 2020/0015818 A1 | 1/2020 | Amariglio et al. |
| 2020/0046362 A1 | 2/2020 | Baril et al. |
| 2020/0093486 A1 | 3/2020 | Somekh et al. |
| 2020/0222046 A1 | 7/2020 | Somekh et al. |
| 2021/0007740 A1 | 1/2021 | Marecki et al. |
| 2021/0085323 A1 | 3/2021 | Somekh et al. |
| 2021/0346021 A1 | 11/2021 | Amariglio et al. |
| 2022/0183688 A1 | 6/2022 | Moy et al. |
| 2022/0338874 A1 | 10/2022 | Marecki et al. |
| 2022/0387025 A1 | 12/2022 | Marecki et al. |
| 2023/0092719 A1 | 3/2023 | Marbach et al. |
| 2023/0165584 A1 | 6/2023 | Leimbach et al. |
| 2023/0233208 A1 | 7/2023 | Marecki et al. |
| 2024/0050093 A1 | 2/2024 | Marecki et al. |
| 2025/0009352 A1 | 1/2025 | Marecki et al. |

FOREIGN PATENT DOCUMENTS

| | | |
|---|---|---|
| CN | 101507643 A | 8/2009 |
| CN | 101664331 A | 3/2010 |
| CN | 101965156 | 2/2011 |
| CN | 108542464 A | 9/2018 |
| DE | 112019002420 T5 | 3/2021 |
| EP | 1563791 A1 | 8/2005 |
| EP | 1563792 A1 | 8/2005 |
| EP | 1563794 A1 | 8/2005 |
| EP | 1709911 A1 | 10/2006 |
| EP | 1021130 | 11/2006 |
| EP | 1908410 | 4/2008 |
| EP | 2253277 A1 | 11/2010 |
| EP | 2253278 A1 | 11/2010 |
| EP | 2586382 | 9/2013 |
| EP | 2777530 | 9/2014 |
| EP | 2839786 A1 | 2/2015 |
| EP | 2886020 | 6/2015 |
| EP | 2886071 | 6/2015 |
| EP | 2484290 B1 | 7/2015 |
| EP | 2942022 | 11/2015 |
| EP | 2311385 B1 | 5/2017 |
| WO | 2004075728 A2 | 9/2004 |
| WO | 2016/107586 | 7/2016 |
| WO | 2018035796 A1 | 3/2018 |

OTHER PUBLICATIONS

International Search Report and Written Opinion dated Jun. 18, 2018 for PCT Application No. PCT/US2018/025988 filed Apr. 4, 2018, 9 pages.
International Search Report and Written Opinion dated May 25, 2023 for PCT Application No. PCT/US2023/014366 filed Mar. 2, 2013, 8 pages.
International Search Report and Written Opinion dated Oct. 22, 2018 for PCT Application No. PCT/ US2018/038909 filed Jun. 22, 2018, 10 pages.
International Search Report and Written Opinion dated Oct. 4, 2019 for PCT Application No. PCT/US2019/040315 filed Jul. 2, 2018, 9 pages.
Final Office Action received in U.S. Appl. No. 15/481,949 dated May 29, 2019, 15 pages.

(56) References Cited

OTHER PUBLICATIONS

International Search Report and Written Opinion received in PCT/US2022/032434 dated Oct. 19, 2022, 11 pages.
Non Final Office Action received in U.S. Appl. No. 15/481,949 dated Mar. 18, 2019, 22 pages.
Non Final Office Action received in U.S. Appl. No. 16/249,520 dated Jul. 27, 2020, 10 pages.
Non Final Office Action received in U.S. Appl. No. 17/113,865 dated Sep. 19, 2022, 13 pages.
Non Final Office Action received in U.S. Appl. No. 17/241,538 dated Aug. 16, 2022, 10 pages.
Non Final Office Action received in U.S. Appl. No. 17/382,705 dated Sep. 24, 2024, 10 pages.
Non Final Office Action received in U.S. Appl. No. 17/686,730 dated Jan. 8, 2024, 10 pages.
Non Final Office Action received in U.S. Appl. No. 18/129,324 dated Jan. 19, 2024, 9 pages.
Notice of Allowance received in U.S. Appl. No. 16/249,520 dated Nov. 3, 2020, 8 pages.
Notice of Allowance received in U.S. Appl. No. 16/577,097 dated Sep. 13, 2021, 8 pages.
Notice of Allowance received in U.S. Appl. No. 16/582,829 dated May 14, 2021, 7 pages.
Notice of Allowance received in U.S. Appl. No. 17/133,865 dated Dec. 7, 2022; 9 pages.
Notice of Allowance received in U.S. Appl. No. 17/241,538 dated Jan. 11, 2023, 9 pages.
Notice of Allowance received in U.S. Appl. No. 17/686,730 dated Apr. 16, 2024, 7 pages.
Notice of Allowance received in U.S. Appl. No. 17/686,730 dated Aug. 5, 2024, 8 pages.
Notice of Allowance received in U.S. Appl. No. 18/129,324 dated May 15, 2024, 7 pages.
Notice of Allowance received in U.S. Appl. No. 15/481,949 dated Aug. 14, 2019, 10 pages.
Restriction Requirement received in U.S. Appl. No. 17/382,705 dated May 8, 2024, 6 pages.
Restriction Requirement received in U.S. Appl. No. 18/496,107 dated Sep. 24, 2024, 14 pages.
International Search Report and Written Opinion received in PCT App No. PCT/US24/52666 dated Dec. 20, 2024.
Non-Final Office Action received in U.S. Appl. No. 18/496,107 dated Dec. 12, 2024, 55 pages.
Non-Final Office Action received in U.S. Appl. No. 17/833,302 dated Jan. 30, 2025, 51 pages.

* cited by examiner

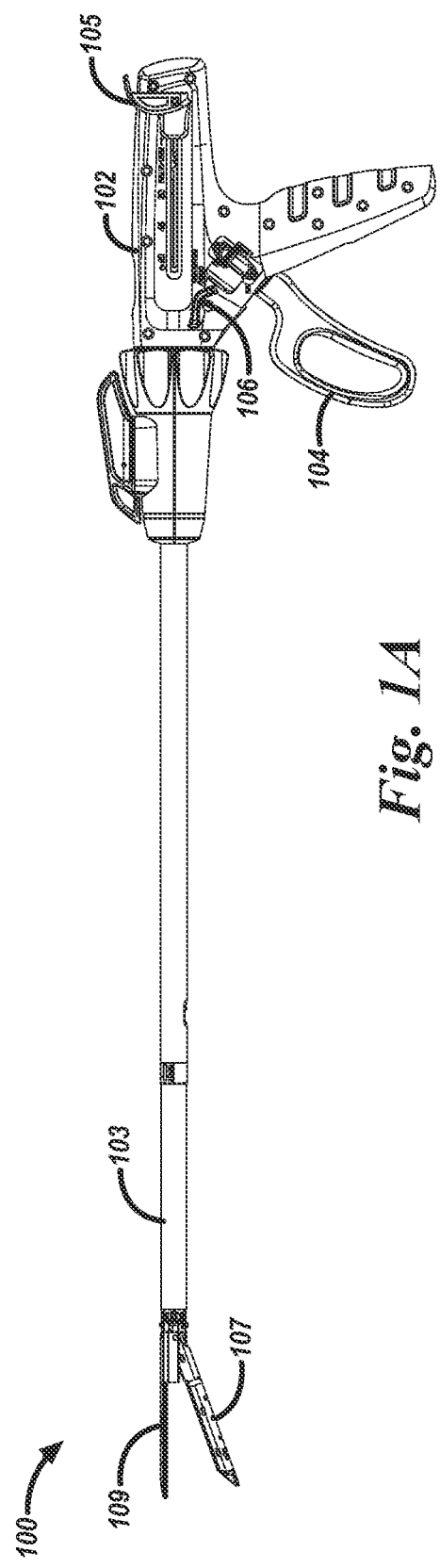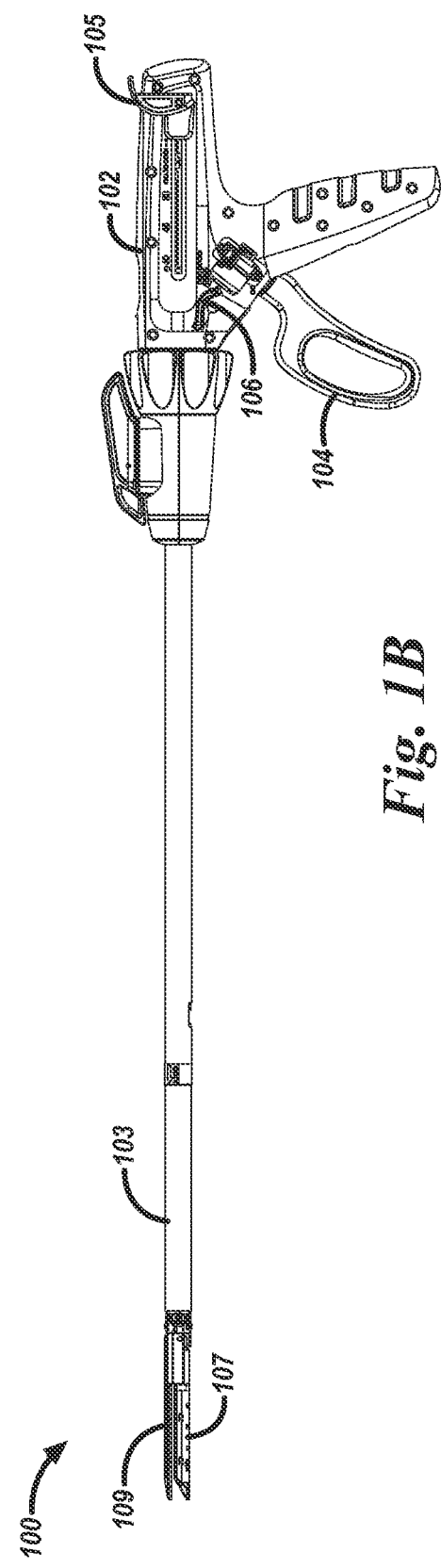

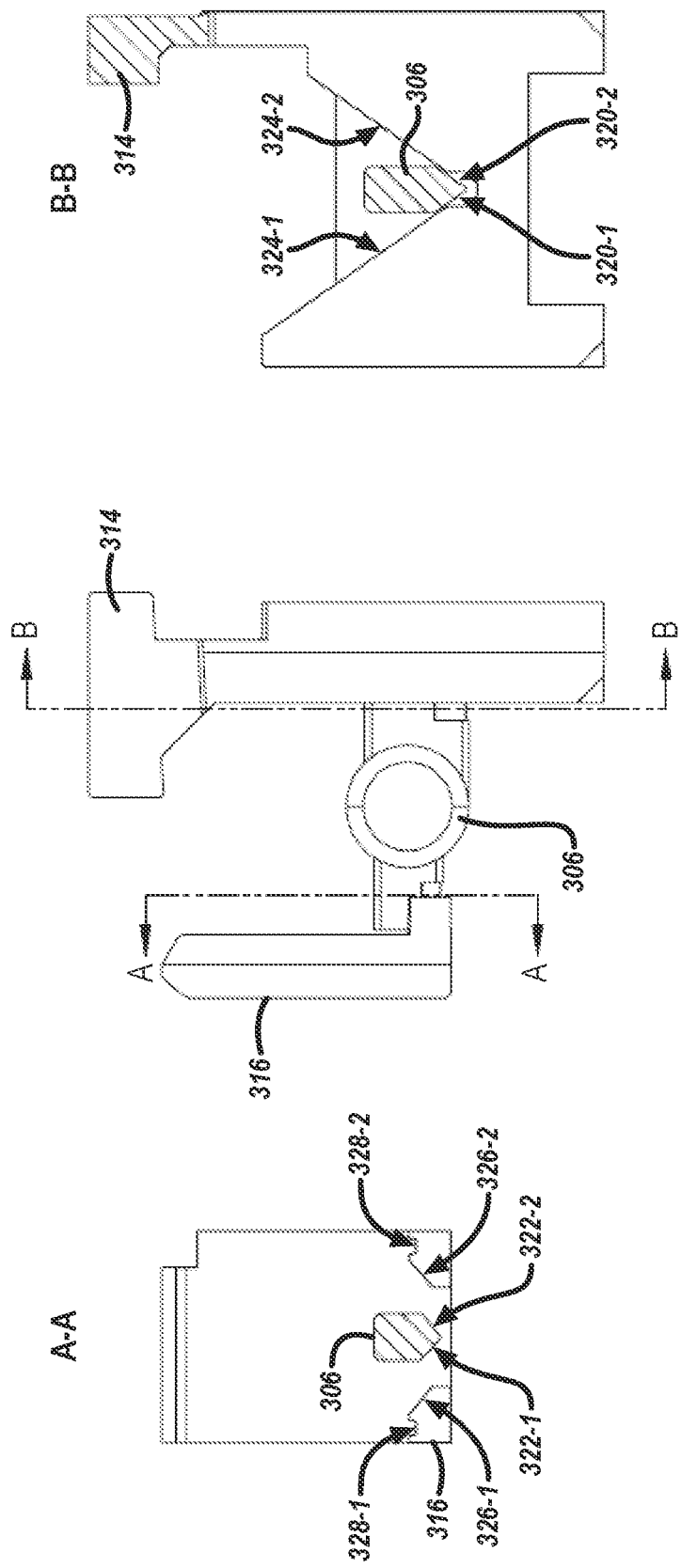

ADVANCING A TOOTHED RACK OF A SURGICAL HANDLE ASSEMBLY

CROSS REFERENCE TO RELATED APPLICATION

This application is a continuation of U.S. application Ser. No. 17/113,865, filed Dec. 7, 2020, issued as U.S. Pat. No. 11,617,583, which is a continuation of U.S. application Ser. No. 16/249,520, filed Jan. 16, 2019, issued as U.S. Pat. No. 10,856,871, which the present application claims the benefit of and priority to and are hereby incorporated herein by reference in their entirety.

TECHNICAL FIELD

The present disclosure relates generally to a surgical handle assembly, and more particularly, to advancing a toothed rack of a surgical handle assembly.

BACKGROUND

A surgical handle assembly can be used in a number of surgical devices. One example includes use as a surgical stapler. A surgical stapler is a fastening device used to clamp tissue between opposing jaw structures to join tissue using surgical fasteners. Surgical staplers can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. A row of staples can have a linear length between 30 mm and 60 mm, for example. A staple can be ejected by actuation of a movable handle member that is a part of the surgical handle assembly of the surgical stapler.

BRIEF DESCRIPTION OF THE DRAWINGS

FIG. 1A is a schematic diagram of a surgical stapling apparatus including a surgical handle assembly and a reloadable cartridge assembly in an unclamped position in accordance with a number of embodiments of the present disclosure.

FIG. 1B is a schematic diagram of a surgical stapling apparatus including a surgical handle assembly and a reloadable cartridge assembly in a clamped position in accordance with a number of embodiments of the present disclosure.

FIG. 3 is a schematic diagram of a safety latch, a button, and a disengagement mechanism in accordance with a number of embodiments of the present disclosure.

DETAILED DESCRIPTION

Figure 2A:
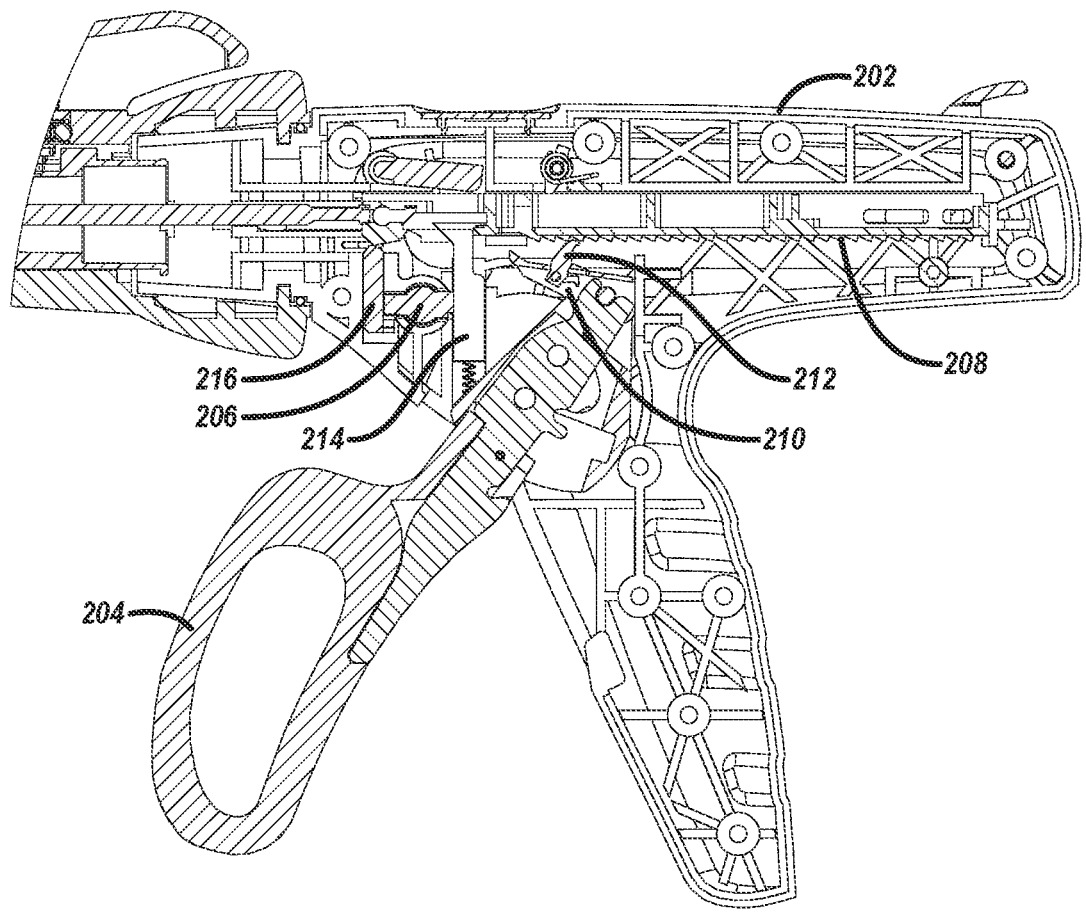
FIG. 2A is a schematic diagram of a surgical handle assembly in an unclamped position including a movable handle member, a button, a toothed rack, a driving pawl, a latch, a disengagement mechanism, and a safety latch in accordance with a number of embodiments of the present disclosure.

The present disclosure includes apparatuses for a surgical handle assembly. An example apparatus includes a toothed rack, a movable handle member, a driving pawl configured to engage the toothed rack and advance the toothed rack in a linear distal direction in response to a movable handle member advancing in a proximal direction and a latch configured to engage the toothed rack and advance the toothed rack in a linear proximal direction in response to the movable handle member advancing in a distal direction.

Use of the surgical handle assembly with a surgical stapler coupled to a reloadable cartridge can advance the reloadable cartridge to a clamped position in response to the driving pawl advancing the toothed rack in the linear distal direction and the reloadable cartridge can advance to an unclamped position in response to the latch advancing the toothed rack in the linear proximal direction.

For example, a user can move the movable handle member from a most distal position to a most proximal position. This movement can cause the driving pawl to engage the toothed rack, drive it distally to cause the elongated members of the reloadable cartridge assembly to clamp and can cause the latch to enter a slot in the toothed rack. While the toothed rack is moving distally, a safety latch can move downward and upward in response to the movement of the toothed rack and the latch can move into engagement with the toothed rack such that the toothed rack cannot be moved distally either with the movable handle member or manually by the user using retract grips. At this stage, the user can either push a button such that staples can be delivered or release the movable handle member to cause the elongated members of the reloadable cartridge assembly to unclamp.

If the user does not push the button, but instead releases the movable handle member, the movable handle member can move in a distal direction and stop at a position between the most distal position and the most proximal position. In response to the movable handle member moving in the distal direction, the latch can engage the toothed rack and can drive the toothed rack in the linear proximal direction causing the elongated members of the reloadable cartridge assembly to unclamp.

In some examples, the user can move the movable handle member from the position between the most distal position and the most proximal position to the most proximal position. The elongated members of the reloadable cartridge assembly can clamp in response to the user moving the movable handle member from the position between the most distal position and the most proximal position to the most proximal position. Alternatively, the user can move the movable handle member from the position between the most distal position and the most proximal position to the distal most position and then, upon moving the movable handle member in the proximal direction, clamp the elongated members of the reloadable cartridge assembly.

In a number of embodiments, the surgical handle assembly with the surgical stapler coupled to the reloadable cartridge can deploy a number of staples. The reloadable cartridge can deploy the number of staples in response to a user pressing the button and moving the movable handle member in the proximal direction. In some examples, the movable handle member can be in the most proximal position or a position between the most proximal position and the most distal position when the button is pressed by the user.

The button can include a first slanted surface. When the button is pressed and the button is in a pressed position, the first slanted surface of the button can cause a safety latch to move in a downward direction. Once the safety latch is in a lowered position, the safety latch can no longer engage the toothed rack to prevent the toothed rack from moving further in the linear distal direction such that the staples can be delivered.

The button can also include a second slanted surface. When the button is pressed and the button is in the pressed position the second slanted surface of the button can contact a disengagement mechanism and cause the disengagement mechanism to move in a downward direction. As the disengagement mechanism moves downward, it can contact the driving pawl and move the driving pawl and latch in a downward direction to prevent the driving pawl and the latch from engaging the toothed rack.

In a number of embodiments, the movable handle member can be coupled to a spring. The spring can bias the movable handle member to the most proximal position. In response to the disengagement mechanism preventing the latch from engaging the toothed rack, the spring can bias the movable handle member to the most distal position without advancing the toothed rack in the linear proximal direction. Without advancing the toothed rack in the linear proximal direction, the reloadable cartridge can stay in the clamped position.

A user can advance the movable handle member from the most distal position to the most proximal position. The driving pawl can reengage with the toothed rack and advance the toothed rack in a linear distal direction in response to the movable handle member advancing in the proximal direction. The safety latch, in the lowered position, can no longer engage the toothed rack to prevent the toothed rack from moving further in the linear distal direction such that the staples can be delivered.

When the user has finished delivering staples, the user can manually move the toothed rack in the linear proximal direction. In some examples, the user can manually move the toothed rack in the linear proximal direction by engaging retract grips on both sides of the surgical handle assembly and pulling the retract grips in the linear proximal direction to cause the toothed rack, the button, the safety latch, the disengagement mechanism, the driving pawl, and the latch to return to a start position.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "X", "Y", "N", "M", etc., particularly with respect to reference numerals in the drawings, indicate that a number of the particular feature so designated can be included. It is also to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of pivot points) can refer to one or more pivot points, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 106 may reference element "6" in FIG. 1, and a similar element may be referenced as 206 in FIG. 2A. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1A is a schematic diagram of a surgical stapling apparatus 100 including a surgical handle assembly 102 and a reloadable cartridge assembly in an unclamped position in accordance with a number of embodiments of the present disclosure. In the example, the surgical stapling apparatus 100 can include a surgical handle assembly 102 and a reloadable cartridge assembly 103.

As shown in the example of FIG. 1A, the reloadable cartridge assembly 103, e.g. a disposable loading unit, can be releasably secured to a distal end of an elongated body of the surgical handle assembly 102. In this example, the reloadable cartridge assembly 103 can include a first elongated member 107 and a second elongated member 109. The reloadable cartridge assembly 103 can be in a clamped position when the first elongated member 107 and the second elongated member 109 are clamping tissue and/or contacting each other. The reloadable cartridge assembly 103 can be in an unclamped position when the first elongated member 107 and the second elongated member 109 are not clamping tissue and/or are not in contact with each other.

In a number of embodiments, one of the elongated members can house one or more staple cartridges. The other elongated member can have an anvil that can be used to form a staple when driven from the staple cartridge. As mentioned, a surgical stapling apparatus 100 can receive reloadable cartridge assemblies having rows of staples. In a number of embodiments, third party reloadable cartridge and/or reloadable cartridge assemblies may be used with the surgical handle assembly 102 and embodiments of surgical handle assembly 102 may be configured to receive the same.

The surgical handle assembly 102 coupled to the reloadable cartridge assembly 103 can advance the reloadable cartridge assembly 103 to the clamped position in response to the user actuating the movable handle member 104 of the surgical handle assembly 102 in a proximal direction. The user can also advance the reloadable cartridge assembly 103 to the unclamped position in response to the user actuating the movable handle member 104 in a distal direction.

In a number of embodiments, the surgical handle assembly 102 coupled to the reloadable cartridge assembly 103 can deploy a number of staples. The reloadable cartridge assembly 103 can deploy the number of staples in response to the user pressing a button 106 and moving the movable handle member 104 to the most proximal position. The button 106 can be pushed from either the right-hand side or the left-hand side of the surgical handle assembly 102. The movable handle member 104 can be in the most proximal position when the movable handle member 104 cannot move further in the proximal direction.

When the button 106 is pressed the reloadable cartridge assembly 103 is no longer prevented from delivering the number of staples. Once the button 106 is in the pressed position the number of staples can be ejected in response to the user actuating the movable handle member 104 in the proximal direction.

When the button 106 is pressed the movable handle member 104 is free to move to the most distal position. The movable handle member 104 is in the most distal position when the movable handle member 104 cannot move further in the distal direction. When the button 106 is pressed it also allows the reloadable cartridge assembly 103 to stay in the clamped position even when the movable handle member 104 moves to the most distal position.

A user can advance the movable handle member 104 from the most distal position to the most proximal position. Since the user has pressed the button 106 and the reloadable cartridge assembly 103 is no longer prevented from delivering the number of staples, the number of staples can be delivered in response to the user advancing the movable handle member 104 in the proximal direction.

When the user has finished delivering staples, the user can return the surgical handle assembly 102 and the reloadable cartridge assembly 103 to a start position. In the start position, the button 106 can be in an unpressed position, the movable handle member 104 can be in the most distal position, and the reloadable cartridge assembly 103 can be in an unclamped position. The user can return the surgical handle assembly 102 and the reloadable cartridge assembly 103 to the start position by engaging retract grips 105 on both sides of the surgical handle assembly 102 and pulling the retract grips 105 in the linear proximal direction. In some examples, the retract grips 105 can be used in response to the surgical stapling apparatus 100 failing to unclamp.

The surgical handle assembly 102 is described with the surgical stapling apparatus 100 example throughout the present disclosure for ease of understanding and illustration. However, embodiments are not limited to use with a surgical stapling apparatus 100.

FIG. 1B is a schematic diagram of a surgical stapling apparatus 100 including a surgical handle assembly 102 and a reloadable cartridge assembly 103 in a clamped position in accordance with a number of embodiments of the present disclosure.

As shown in the example of FIG. 1B, the reloadable cartridge assembly 103, e.g. a disposable loading unit, can be releasably secured to a distal end of an elongated body of the surgical handle assembly 102. In this example, the reloadable cartridge assembly 103 can include a first elongated member 107 and a second elongated member 109. The reloadable cartridge assembly 103 can be in a clamped position when the first elongated member 107 and the second elongated member 109 are clamping tissue and/or contacting each other. The reloadable cartridge assembly 103 can be in an unclamped position when the first elongated member 107 and the second elongated member 109 are not clamping tissue and/or are not in contact with each other.

In a number of embodiments, one of the elongated members can house one or more staple cartridges. The other elongated member can have an anvil that can be used to form a staple when driven from the staple cartridge. As mentioned, a surgical stapling apparatus 100 can receive reloadable cartridge assemblies having rows of staples. In a number of embodiments, third party reloadable cartridge and/or reloadable cartridge assemblies may be used with the surgical handle assembly 102 and embodiments of surgical handle assembly 102 may be configured to receive the same.

The surgical handle assembly 102 coupled to the reloadable cartridge assembly 103 can advance the reloadable cartridge assembly 103 to the clamped position in response to the user actuating the movable handle member 104 of the surgical handle assembly 102 in a proximal direction. The user can also advance the reloadable cartridge assembly 103 to the unclamped position in response to the user actuating the movable handle member 104 in a distal direction.

In a number of embodiments, the surgical handle assembly 102 coupled to the reloadable cartridge assembly 103 can deploy a number of staples. The reloadable cartridge assembly 103 can deploy the number of staples in response to the user pressing a button 106 and moving the movable handle member 104 to the most proximal position. The button 106 can be pushed from either the right-hand side or the left-hand side of the surgical handle assembly 102. The movable handle member 104 can be in the most proximal position when the movable handle member 104 cannot move further in the proximal direction.

When the button 106 is pressed the reloadable cartridge assembly 103 is no longer prevented from delivering the number of staples. Once the button 106 is pressed the number of staples can be ejected in response to the user actuating the movable handle member 104 in the proximal direction.

When the button 106 is pressed the movable handle member 104 is free to move to the most distal position. The movable handle member 104 is in the most distal position when the movable handle member 104 cannot move further in the distal direction. When the button 106 is pressed it also allows the reloadable cartridge assembly 103 to stay in the clamped position even when the movable handle member 104 moves to the most distal position.

A user can advance the movable handle member 104 from the most distal position to the most proximal position. Since the user has pressed the button 106 and the reloadable cartridge assembly 103 is no longer prevented from delivering the number of staples, the number of staples can be delivered in response to the user advancing the movable handle member 104 in the proximal direction.

When the user has finished delivering staples, the user can return the surgical handle assembly 102 and the reloadable cartridge assembly 103 to a start position. In the start position, the button 106 can be in an unpressed position, the movable handle member 104 can be in the most distal position, and the reloadable cartridge assembly 103 can be in an unclamped position. The user can return the surgical handle assembly 102 and the reloadable cartridge assembly 103 to the start position by engaging retract grips 105 on both sides of the surgical handle assembly 102 and pulling the retract grips 105 in the linear proximal direction. In some examples, the retract grips 105 can be used in response to the surgical stapling apparatus 100 failing to unclamp.

The surgical handle assembly 102 is described with the surgical stapling apparatus 100 example throughout the present disclosure for ease of understanding and illustration. However, embodiments are not limited to use with a surgical stapling apparatus 100.

FIG. 2A is a schematic diagram of a surgical handle assembly 202 in an unclamped position including a movable handle member 204, a button 206, a toothed rack 208, a driving pawl 210, a latch 212, a disengagement mechanism 214, and a safety latch 216 in accordance with a number of embodiments of the present disclosure.

The surgical handle assembly 202 can be in a home unclamped position when the movable handle member 204 is not being actuated by the user and the reloadable cartridge assembly (e.g., reloadable cartridge assembly 103 in FIG. 1) is in an unclamped position. The movable handle member 204 is not being actuated by the user when the movable handle member 204 is in the farthest distal position the movable handle member 204 can travel.

The driving pawl 210 can be coupled to the movable handle member 204. In some examples, the driving pawl 210 can be coupled to the movable handle member 204 via a pin, which can allow the driving pawl 210 to pivot and engage or disengage from the toothed rack 208. The toothed rack 208 can be in a home position when the toothed rack 208 is in a linear most proximal position. When the toothed rack 208 is in the home position, the driving pawl 210 can be disengaged from the toothed rack 208.

The latch 212 can be coupled to the driving pawl 210. The latch 212 can pivot via a pin coupling the latch 212 to the driving pawl 210. In some examples, the latch 212 can pivot to engage or disengage from the toothed rack 208. When the toothed rack 208 is in the home position, the latch 212 can be disengaged from the toothed rack 208.

The latch 212 and/or the driving pawl 210 can be disengaged from the toothed rack via the disengagement mechanism 214. The disengagement mechanism 214 can contact the driving pawl 210 to disengage the driving pawl 210 and/or the latch 212 from the toothed rack 208 in response to a user pressing the button 206. However, when the toothed rack 208 is in the home position, the disengagement mechanism 214 may not contact the driving pawl 210.

In some examples, pressing the button 206 can disengage the safety latch 216. When the button 206 is pressed one of the one or more slanted surfaces (e.g., slanted surfaces 322-1, 322-2 in FIG. 3) of the button 206 can contact one or more slanted surfaces (e.g., slanted surface 326-1, 326-2 in FIG. 3) of the safety latch 216 and cause the safety latch 216 to move in a downward direction. In the lowered position, the safety latch 216 cannot engage the toothed rack 208 to prevent the toothed rack 208 from moving further in the linear distal direction such that staples can be delivered.

The safety latch 216 can prevent a user from accidentally ejecting staples. For example, the safety latch 216 can make a user press the button 206 in order to eject staples. In FIG. 2A, the safety latch 216 is biased upward which can prevent staples from being ejected if a user were to actuate the movable handle member 104 to the proximal direction.

Figure 2B:
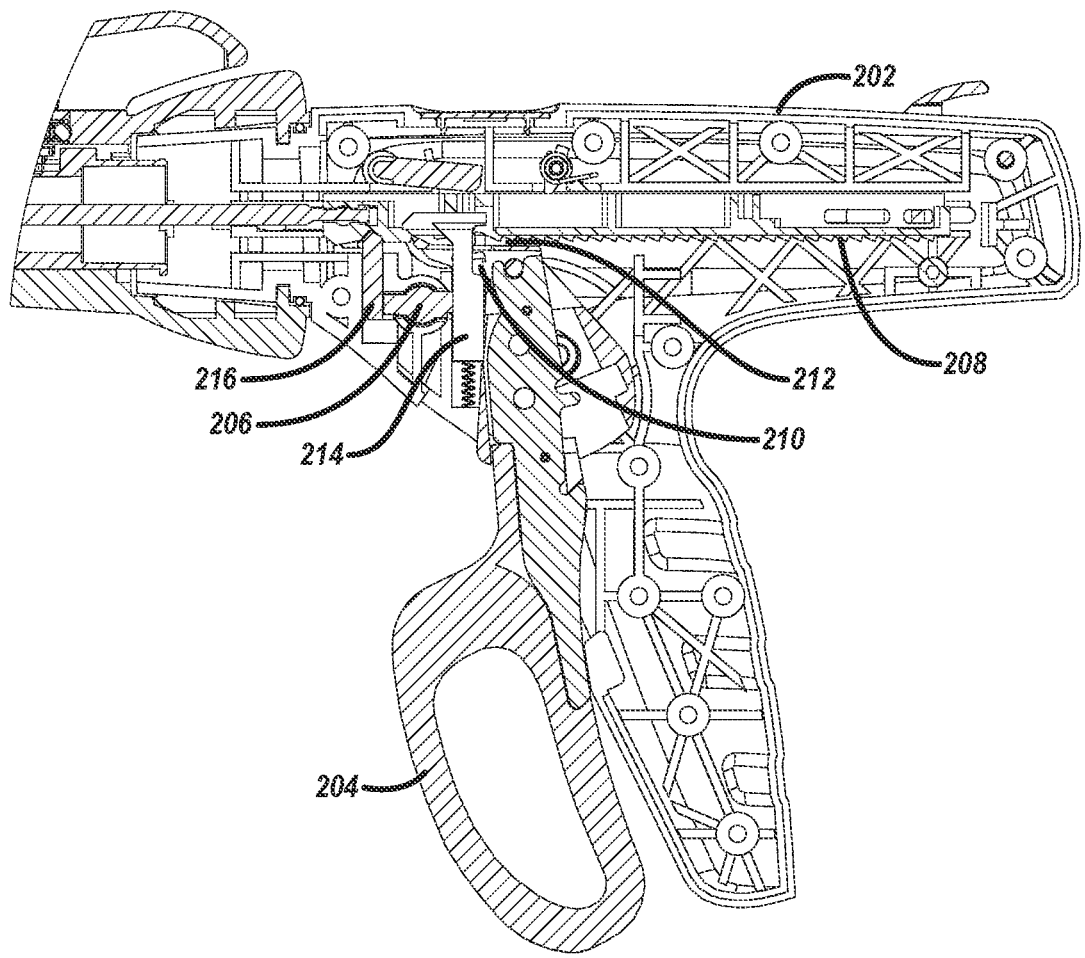
FIG. 2B is a schematic diagram of a surgical handle assembly in a clamped position including a movable handle member, a button, a toothed rack, a driving pawl, a latch, a disengagement mechanism, and a safety latch in accordance with a number of embodiments of the present disclosure.

FIG. 2B is a schematic diagram of a surgical handle assembly 202 in a clamped position including a movable handle member 204, a button 206, a toothed rack 208, a driving pawl 210, a latch 212, a disengagement mechanism 214, and a safety latch 216 in accordance with a number of embodiments of the present disclosure.

The surgical handle assembly 202 can be in an index clamped position when the movable handle member 204 is fully actuated by the user and the reloadable cartridge assembly (e.g., reloadable cartridge assembly 103 in FIG. 1) is in a clamped position. For example, the movable handle member 204 can be fully actuated by the user squeezing the movable handle member 204 in a proximal direction from the most distal position, shown in FIG. 2A, until the movable handle member 204 cannot travel any further in the proximal direction.

As previously described in FIG. 2A, the driving pawl 210 can be coupled to the movable handle member 204 via a pin, which can allow the driving pawl 210 to pivot and engage or disengage from the toothed rack 208. For example, the driving pawl 210 can be configured to engage the toothed rack 208 and advance the toothed rack 208 in a linear distal direction in response to the movable handle member 204 advancing in the proximal direction. In some examples, the surgical handle assembly 202 can advance the reloadable cartridge assembly (e.g., reloadable cartridge assembly 103 in FIG. 1) to a clamped position in response to the driving pawl 210 advancing the toothed rack 208 in the linear distal direction.

The latch 212, as previously described in FIG. 2A, can pivot from the driving pawl 210 to engage or disengage from the toothed rack 208. When the toothed rack 208 is in the index position, the latch 212 can engage the toothed rack 208.

The disengagement mechanism 214 can contact the driving pawl 210 to disengage the driving pawl 210 and/or the latch 212 from the toothed rack. In FIG. 2B, the disengagement mechanism 214 is not in contact with the driving pawl 210.

The driving pawl 210 can be disengaged from the toothed rack 208 in response to a user pressing the button 206. The button 206 can include one or more slanted surfaces (e.g., slanted surfaces 320, 322 in FIG. 3). When the button 206 is pressed one of the one or more slanted surfaces of the button 206 can contact a surface of the disengagement mechanism 214 and cause the disengagement mechanism 214 to move in a downward direction. As the disengagement mechanism 214 moves downward, the disengagement mechanism 214 can contact the driving pawl 210 and move the driving pawl 210 and the latch 212 in a downward direction to prevent the driving pawl 210 and the latch 212 from engaging the toothed rack 208. In FIG. 2B, the button 206 is not in a pressed position.

In some examples, pressing the button 206 can disengage the safety latch 216. When the button 206 is pressed one of the one or more slanted surfaces (e.g., slanted surfaces 322-1, 322-2 in FIG. 3) of the button 206 can contact one or more slanted surfaces (e.g., slanted surface 326-1, 326-2 in FIG. 3) of the safety latch 216 and cause the safety latch 216 to move in a downward direction. In the lowered position, the safety latch 216 cannot engage the toothed rack 208 to prevent the toothed rack 208 from moving further in the linear distal direction such that staples can be delivered.

As previously described in FIG. 2A, the safety latch 216 can prevent a user from accidentally ejecting staples. For example, the safety latch 216 can make a user press the button 206 in order to eject staples. In FIG. 2B, the movable handle member 204 is in a most proximal position, but staples are not ejected because the safety latch 216 is in an upward position preventing the toothed rack 208 from moving further in the linear distal direction. The toothed rack 208 can include an opening, for example a slot. The safety latch 216 in the upward position can enter the opening of the toothed rack 208, as shown in FIG. 2B. In some examples, the safety latch 216 engaged in the opening of the toothed rack 208 can maintain the surgical handle assembly 202 in a clamped position.

Figure 2C:
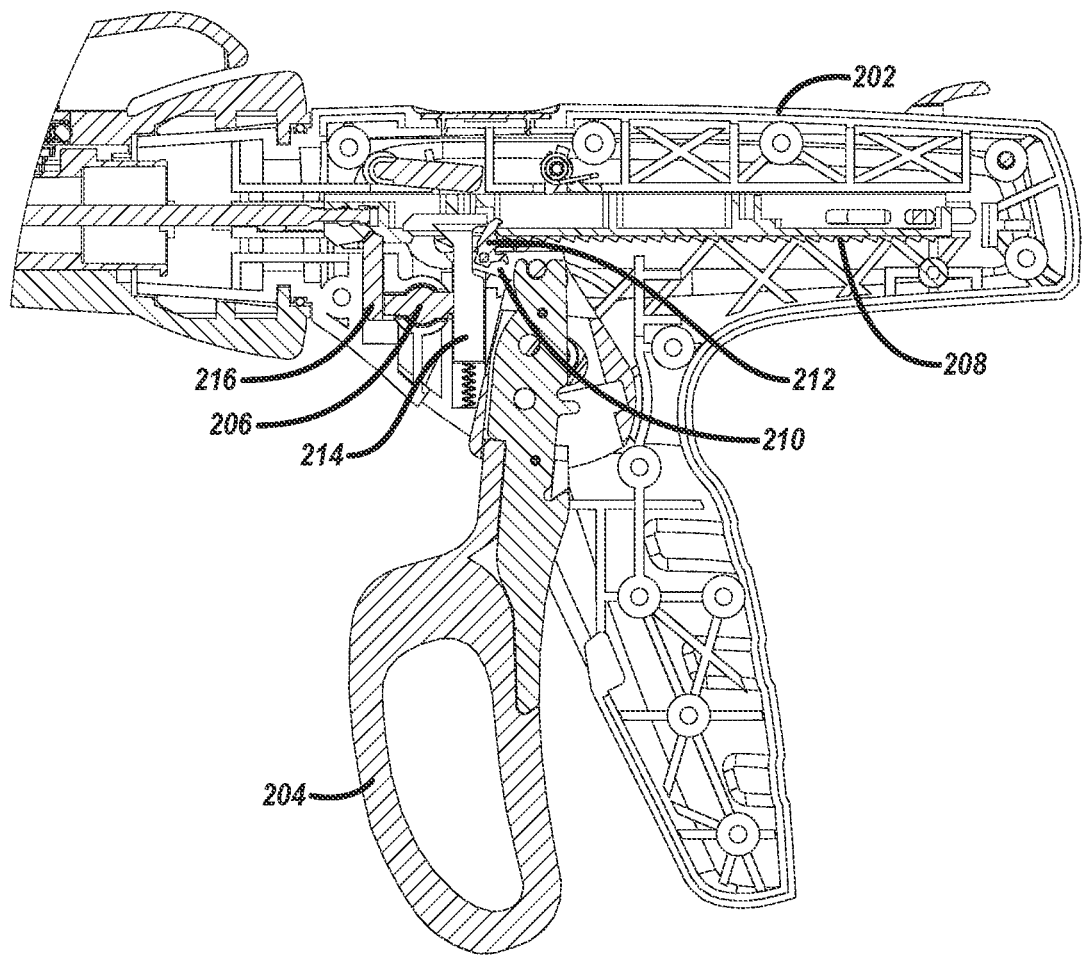
FIG. 2C is a schematic diagram of a surgical handle assembly in a clamped position including a movable handle member, a button, a toothed rack, a driving pawl, a latch, a disengagement mechanism, and a safety latch in accordance with a number of embodiments of the present disclosure.

FIG. 2C is a schematic diagram of a surgical handle assembly 202 in a clamped position including a movable handle member 204, a button 206, a toothed rack 208, a driving pawl 210, a latch 212, a disengagement mechanism 214, and a safety latch 216 in accordance with a number of embodiments of the present disclosure.

The surgical handle assembly 202 can be in a clamped position between a most distal position and a most proximal position when the movable handle member 204 is partially actuated by the user and the reloadable cartridge assembly (e.g., reloadable cartridge assembly 103 in FIG. 1) is in a clamped position. In some examples, the movable handle member 204 can remain in the position between the most distal position and the most proximal position without any assistance from the user. This position can be, but is not limited to, halfway between the most distal position and the most proximal position.

As previously described in FIG. 2A, the driving pawl 210 can be coupled to the movable handle member 204 via a pin, which can allow the driving pawl 210 to pivot and engage or disengage from the toothed rack 208. When the toothed rack 208 is between the linear most proximal position and the linear most distal position, the driving pawl 210 can be disengaged from the toothed rack 208. For example, the driving pawl 210 can be disengaged from the toothed rack 208 to allow the toothed rack 208 to move in a linear proximal direction in response to the movable handle member 204 moving in a distal direction.

The latch 212, as previously described in FIG. 2A, can pivot from the driving pawl 210 to engage or disengage from the toothed rack 208. In the clamped position, where the movable handle member 204 is between the most distal position and the most proximal position, the latch 212 can engage the toothed rack 208. The latch 212 can cause the toothed rack 208 to advance in the linear proximal direction in response to the user moving the movable handle member 204 in the distal direction. In some examples, the reloadable cartridge assembly (e.g., reloadable cartridge assembly 103 in FIG. 1) can move to an unclamped position in response to the toothed rack 208 advancing in the linear proximal direction.

The disengagement mechanism 214 can contact the driving pawl 210 to disengage the driving pawl 210 and/or the latch 212 from the toothed rack 208. In FIG. 2C, the disengagement mechanism 214 is not in contact with the driving pawl 210.

The latch 212 can be disengaged from the toothed rack 208 in response to a user pressing the button 206. The button 206 can include one or more slanted surfaces (e.g., slanted surfaces 320-1, 320-2, 322-1, 322-2 in FIG. 3). When the button 206 is pressed one of the one or more slanted surfaces of the button 206 can contact one or more slanted surfaces (e.g., slanted surface 324-1, 324-2 in FIG. 3) of the disengagement mechanism 214 and cause the disengagement mechanism 214 to move in a downward direction. As the disengagement mechanism 214 moves downward, the disengagement mechanism 214 can contact the driving pawl 210 and move the driving pawl 210 and the latch 212 in a downward direction to prevent the latch 212 from engaging the toothed rack 208. In FIG. 2C, the button 206 is not in a pressed position.

In some examples, pressing the button 206 can disengage the safety latch 216. When the button 206 is pressed one of the one or more slanted surfaces (e.g., slanted surfaces 322-1, 322-2 in FIG. 3) of the button 206 can contact one or more slanted surfaces (e.g., slanted surface 326-1, 326-2 in FIG. 3) of the safety latch 216 and cause the safety latch 216 to move in a downward direction. In the lowered position, the safety latch 216 cannot engage the toothed rack 208 to prevent the toothed rack 208 from moving further in the linear distal direction such that staples can be delivered.

The safety latch 216 can prevent a user from accidentally ejecting staples. For example, the safety latch 216 can make the user press the button 206 in order to eject staples. In FIG. 2C, the safety latch 216 is in an upward position that would prevent staples from being ejected if a user were to actuate the movable handle member 204 in the proximal direction. The toothed rack 208 can include an opening, for example a slot. The safety latch 216 in the upward position can enter the opening of the toothed rack 208, as shown in FIG. 2C. In some examples, the safety latch 216 engaged in the opening of the toothed rack 208 can maintain the surgical handle assembly 202 in a clamped position.

Figure 2D:
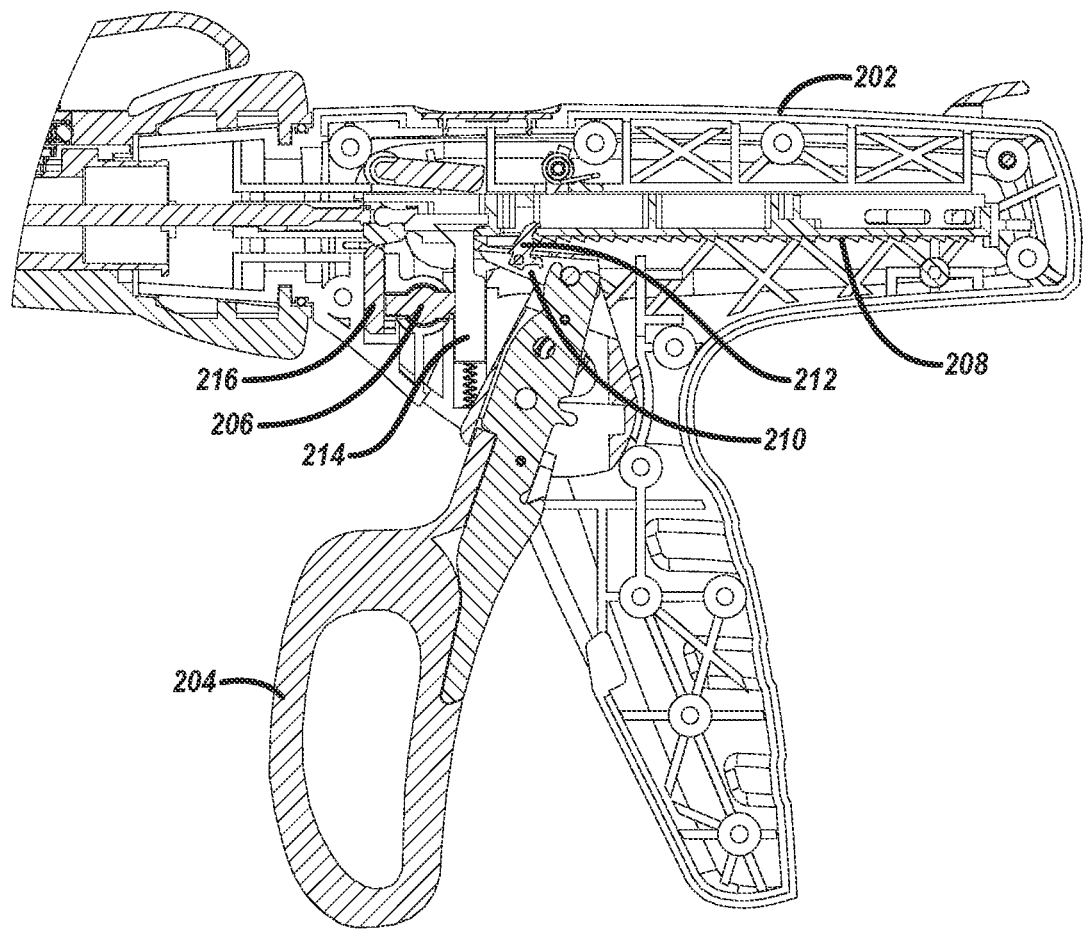
FIG. 2D is a schematic diagram of a surgical handle assembly in an unclamped position including a movable handle member, a button, a toothed rack, a driving pawl, a latch, a disengagement mechanism, and a safety in accordance with a number of embodiments of the present disclosure.

FIG. 2D is a schematic diagram of a surgical handle assembly 202 in an unclamped position including a movable handle member 204, a button 206, a toothed rack 208, a driving pawl 210, a latch 212, a disengagement mechanism 214, and a safety latch 216 in accordance with a number of embodiments of the present disclosure.

The surgical handle assembly 202 can be in an unclamped position with the movable handle member 204 between a most distal position and a most proximal position when the movable handle member 204 is partially actuated by the user and the reloadable cartridge assembly (e.g., reloadable cartridge assembly 103 in FIG. 1) is in an unclamped position. In some examples, the movable handle member 204 can remain in the unclamped position between the most distal position and the most proximal position without any assistance from the user. The unclamped position with the movable handle member 204 between the most distal position and the most proximal position can be, but is not limited to, halfway between the most distal position and the most proximal position.

As previously described in FIG. 2A, the driving pawl 210 can be coupled to the movable handle member 204 via a pin, which can allow the driving pawl 210 to pivot and engage or disengage from the toothed rack 208. In the unclamped position with the movable handle member 204 between the most distal position and the most proximal position, the driving pawl 210 can engage the toothed rack 208. For example, the driving pawl 210 can engage the toothed rack 208 to allow the driving pawl 208 to advance the toothed rack 208 in a linear distal direction in response to the movable handle member 204 moving in the proximal direction towards the index position.

The latch 212, as previously described in FIG. 2A, can pivot from the driving pawl 210 to engage or disengage from the toothed rack 208. The latch 212 can be biased by a spring to engage the toothed rack 208. In some examples, the spring can bias the latch 212 in a counter clockwise direction. In the clamped position with the movable handle member 204 between the most distal position and the most proximal position, the latch 212 can engage the toothed rack 208. The latch 212 can advance the toothed rack 208 in a linear proximal direction in response to the user moving the movable handle member 204 in the distal direction to unclamp.

The disengagement mechanism 214 can contact the driving pawl 210 to disengage the driving pawl 210 and/or the latch 212 from the toothed rack 208. In some examples, in the unclamped position with the movable handle member 204 between the most distal position and the most proximal position, the disengagement mechanism 214 does not contact the driving pawl 210.

The driving pawl 210 can be disengaged from the toothed rack in response to the user pressing the button 206. The button 206 can include one or more slanted surfaces (e.g., slanted surfaces 320-1, 320-2, 322-1, 322-2 in FIG. 3). When the button 206 is pressed, one of the one or more slanted surfaces of the button 206 can contact one or more slanted surfaces (e.g., slanted surface 324-1, 324-2 in FIG. 3) of the disengagement mechanism 214 and cause the disengagement mechanism 214 to move in a downward direction. As the disengagement mechanism 214 moves downward, the disengagement mechanism 214 can contact the driving pawl 210 and move the driving pawl 210 and the latch 212 in a downward direction to prevent the driving pawl 210 and the latch 212 from engaging the toothed rack 208. In FIG. 2D, the button 206 is not in a pressed position.

In FIG. 2D, the safety latch 216 is in the lowered position. In some examples, the safety latch 216 in the lowered position can engage the toothed rack 208 to prevent the toothed rack 208 from moving further in the linear distal direction from the index position.

Figure 2E:
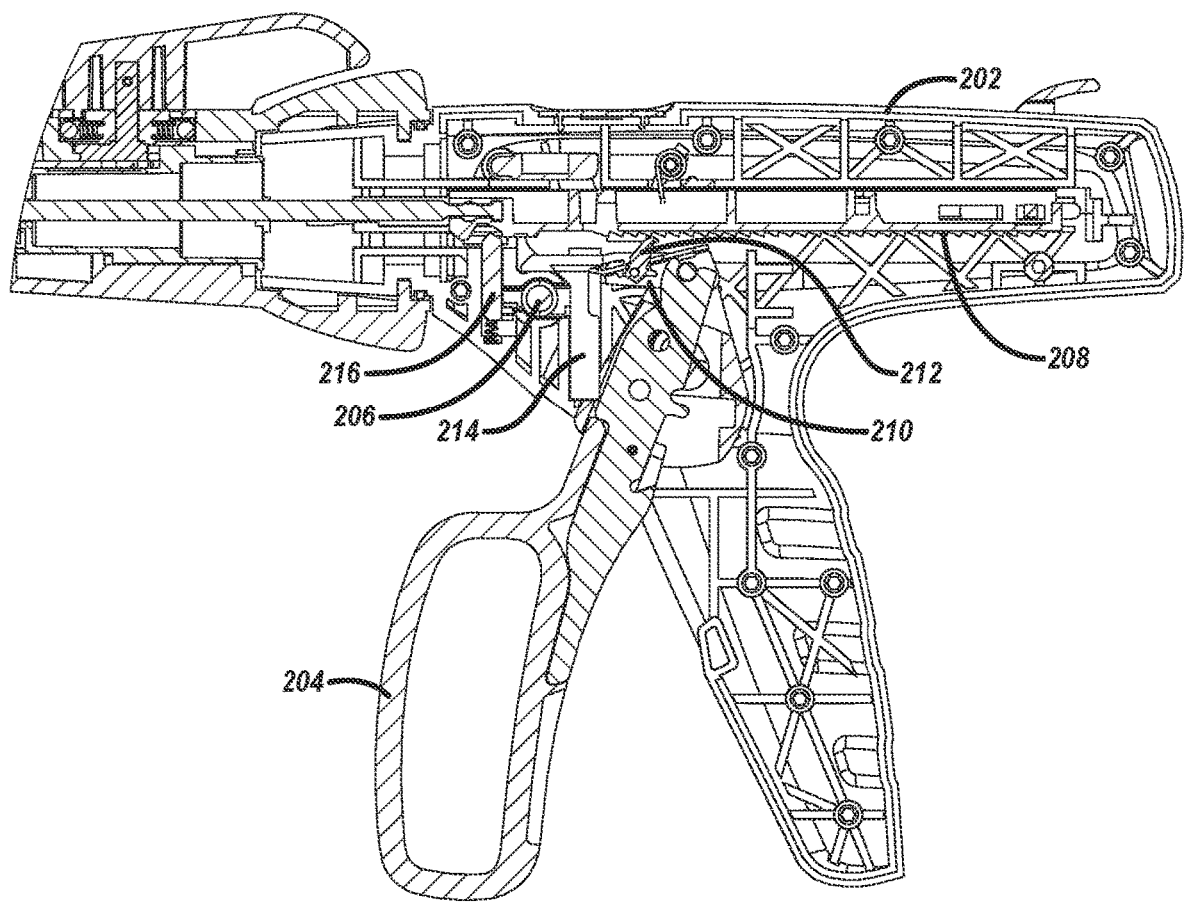
FIG. 2E is a schematic diagram of a surgical handle assembly in an unclamped position including a movable handle member, a button, a toothed rack, a driving pawl, a latch, a disengagement mechanism, and a safety in accordance with a number of embodiments of the present disclosure.

FIG. 2E is a schematic diagram of a surgical handle assembly 202 in a clamped position including a movable handle member 204, a button 206, a toothed rack 208, a driving pawl 210, a latch 212, a disengagement mechanism 214, and a safety latch 216 in accordance with a number of embodiments of the present disclosure.

In FIG. 2E the surgical handle assembly 202 can be transitioning to a ready to fire position and the movable handle member 204 can be in a position between the most distal position and the most proximal position.

When the surgical handle assembly 202 is transitioning to a ready to fire position, the latch 212 can be disengaged from the toothed rack 208 in response to the user pressing the button 206. The button 206 can include one or more slanted surfaces (e.g., slanted surfaces 320-1, 320-2, 322-1, 322-2 in FIG. 3). When the button 206 is pressed one of the one or more slanted surfaces of the button 206 can contact one or more slanted surfaces (e.g., slanted surface 324-1, 324-2 in FIG. 3) of the disengagement mechanism 214 and cause the disengagement mechanism 214 to move in a downward direction. As the disengagement mechanism 214 moves downward, the disengagement mechanism 214 can contact the driving pawl 210 and move the driving pawl 210 and the latch 212 in a downward direction to prevent the latch 212 from engaging the toothed rack 208. In FIG. 2E, the button 206 is in a pressed position.

In FIG. 2E, pressing the button 206 can also disengage the safety latch 216. When the button 206 is pressed one of the one or more slanted surfaces (e.g., slanted surfaces 322-1, 322-2 in FIG. 3) of the button 206 can contact one or more slanted surfaces (e.g., slanted surface 326-1, 326-2 in FIG. 3) of the safety latch 216 and cause the safety latch 216 to move in a downward direction. In the lowered position, the safety latch 216 cannot engage the toothed rack 208 to prevent the toothed rack 208 from moving further in the linear distal direction such that staples can be delivered.

Figure 2F:
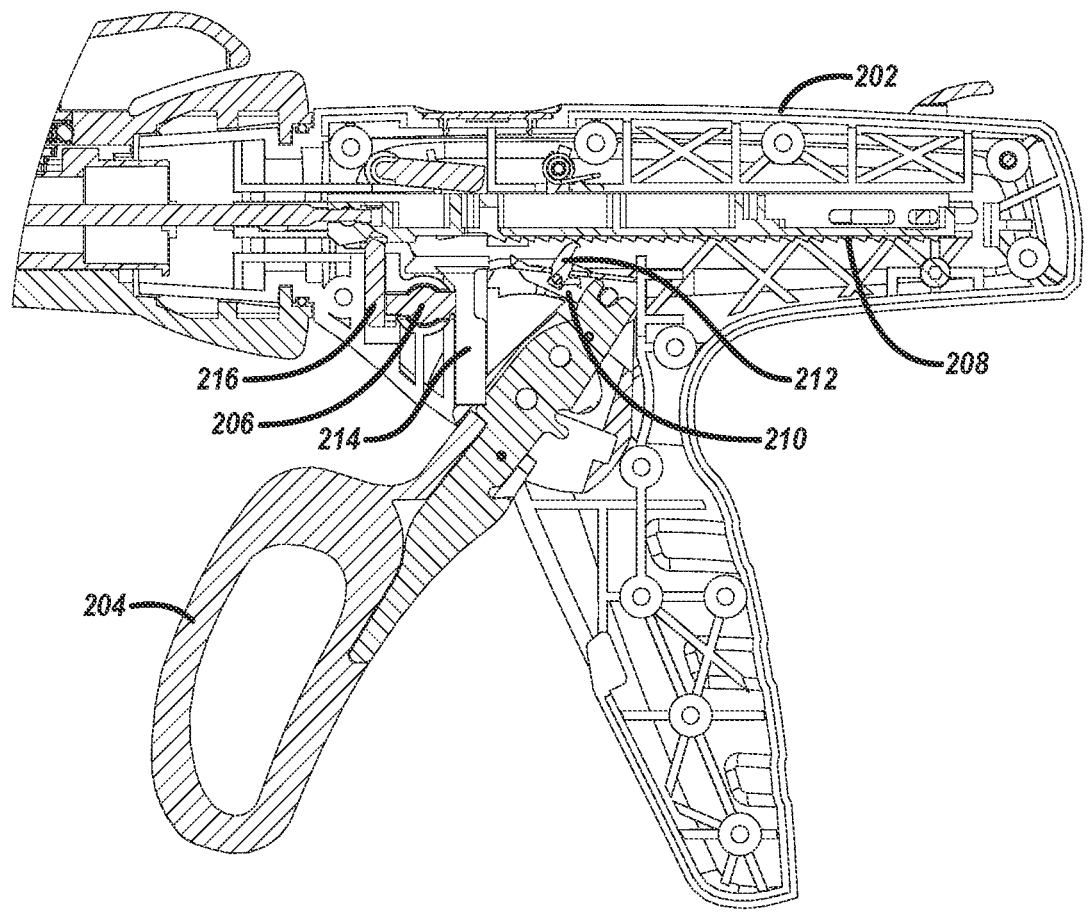
FIG. 2F is a schematic diagram of a surgical handle assembly in an unclamped position including a movable handle member, a button, a toothed rack, a driving pawl, a latch, a disengagement mechanism, and a safety in accordance with a number of embodiments of the present disclosure.

FIG. 2F is a schematic diagram of a surgical handle assembly 202 in a clamped position including a movable handle member 204, a button 206, a toothed rack 208, a driving pawl 210, a latch 212, a disengagement mechanism 214, and a safety latch 216 in accordance with a number of embodiments of the present disclosure.

The surgical handle assembly 202 can be in a ready to fire position when the movable handle member 204 is not being actuated by the user and the reloadable cartridge assembly (e.g., reloadable cartridge assembly 103 in FIG. 1) is in a clamped position. The movable handle member 204 is not being actuated by the user when the movable handle member 204 is in the most distal position.

In the ready to fire position, the driving pawl 210 can be disengaged from the toothed rack 208, the latch 212 can be disengaged from the toothed rack 208, and the disengagement mechanism 214 may not contact the driving pawl 210.

The latch 212 can be disengaged from the toothed rack 208 in response to the user pressing the button 206. The button 206 can include one or more slanted surfaces (e.g., slanted surfaces 320-1, 320-2, 322-1, 322-2 in FIG. 3). When the button 206 is pressed one of the one or more slanted surfaces of the button 206 can contact one or more slanted surfaces (e.g., slanted surface 324-1, 324-2 in FIG. 3) of the disengagement mechanism 214 and cause the disengagement mechanism 214 to move in a downward direction. As the disengagement mechanism 214 moves downward, the disengagement mechanism 214 can contact the driving pawl 210 and move the driving pawl 210 and the latch 212 in a downward direction to prevent the latch 212 from engaging the toothed rack 208. In FIG. 2F, the button 206 is in a pressed position.

In some examples, pressing the button 206 can disengage the safety latch 216. When the button 206 is pressed one of the one or more slanted surfaces (e.g., slanted surfaces 322-1, 322-2 in FIG. 3) of the button 206 can contact one or more slanted surfaces (e.g., slanted surface 326-1, 326-2 in FIG. 3) of the safety latch 216 and cause the safety latch 216 to move in a downward direction. In the lowered position, the safety latch 216 cannot engage the toothed rack 208 to prevent the toothed rack 208 from moving further in the linear distal direction such that staples can be delivered.

The safety latch 216 can prevent a user from accidentally ejecting staples. For example, the safety latch 216 can make the user press the button 206 in order to eject staples. In FIG. 2F, the safety latch 216 is in a downward position that would allow staples to be ejected if a user were to actuate the movable handle member 204 in the proximal direction.

Figure 2G:
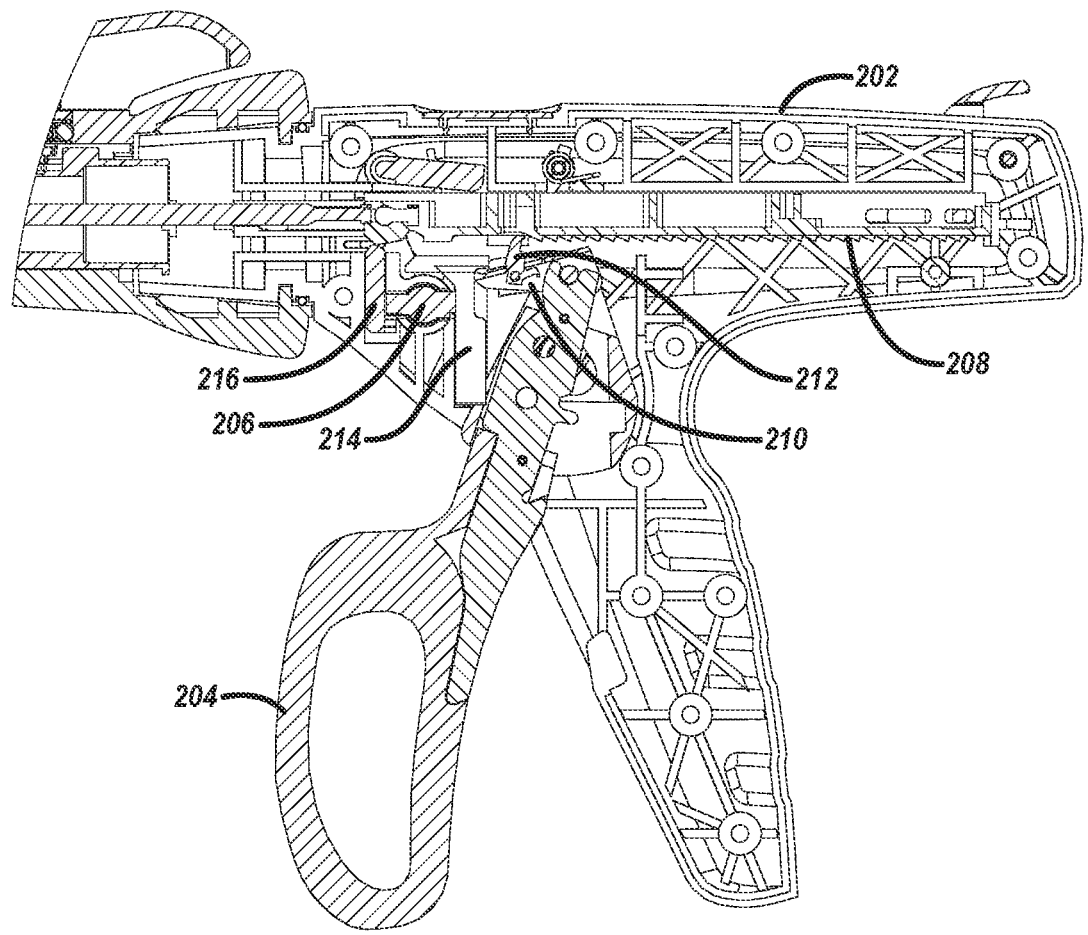
FIG. 2G is a schematic diagram of a surgical handle assembly in an unclamped position including a movable handle member, a button, a toothed rack, a driving pawl, a latch, a disengagement mechanism, and a safety latch in accordance with a number of embodiments of the present disclosure.

FIG. 2G is a schematic diagram of a surgical handle assembly 202 in an unclamped position including a movable handle member 204, a button 206, a toothed rack 208, a driving pawl 210, a latch 212, a disengagement mechanism 214, and a safety latch 216 in accordance with a number of embodiments of the present disclosure.

The surgical handle assembly 202 can be moving from an unclamp position, described in FIG. 2D, to a start position, FIG. 2A, when the disengagement mechanism 214 is lowered in response to a user pressing the button 206.

When the movable handle member 204 is in the position between the most distal position and the most proximal position, the driving pawl 210 can be disengaged from the toothed rack 208, the latch 212 can be disengaged from the toothed rack 208, and the disengagement mechanism 214 can be in contact with the driving pawl 210.

The latch 212 can be disengaged from the toothed rack 208 in response to the user pressing the button 206. The button 206 can include one or more slanted surfaces (e.g., slanted surfaces 320-1, 320-2, 322-1, 322-2 in FIG. 3). When the button 206 is pressed one of the one or more slanted surfaces of the button 206 can contact one or more slanted surfaces (e.g., slanted surface 324-1, 324-2 in FIG. 3) of the disengagement mechanism 214 and cause the disengagement mechanism 214 to move in a downward direction. As the disengagement mechanism 214 moves downward, the disengagement mechanism 214 can contact the driving pawl 210 and move the driving pawl 210 and the latch 212 in a downward direction to prevent the driving pawl 210 and/or the latch 212 from engaging the toothed rack 208. In FIG. 2G, the button 206 is in a pressed position.

In FIG. 2G, the safety latch 216 is biased downwards by the disengagement mechanism 214, such that the one or more slanted surfaces (e.g., slanted surfaces 322-1, 322-2 in FIG. 3) of the button 206 will not contact the one or more slanted surfaces (e.g., slanted surfaces 326-1, 326-2 in FIG. 3) of the safety latch 216 and the safety latch 216 will not move in the downward direction when a user presses the button 206.

Figure 2H:
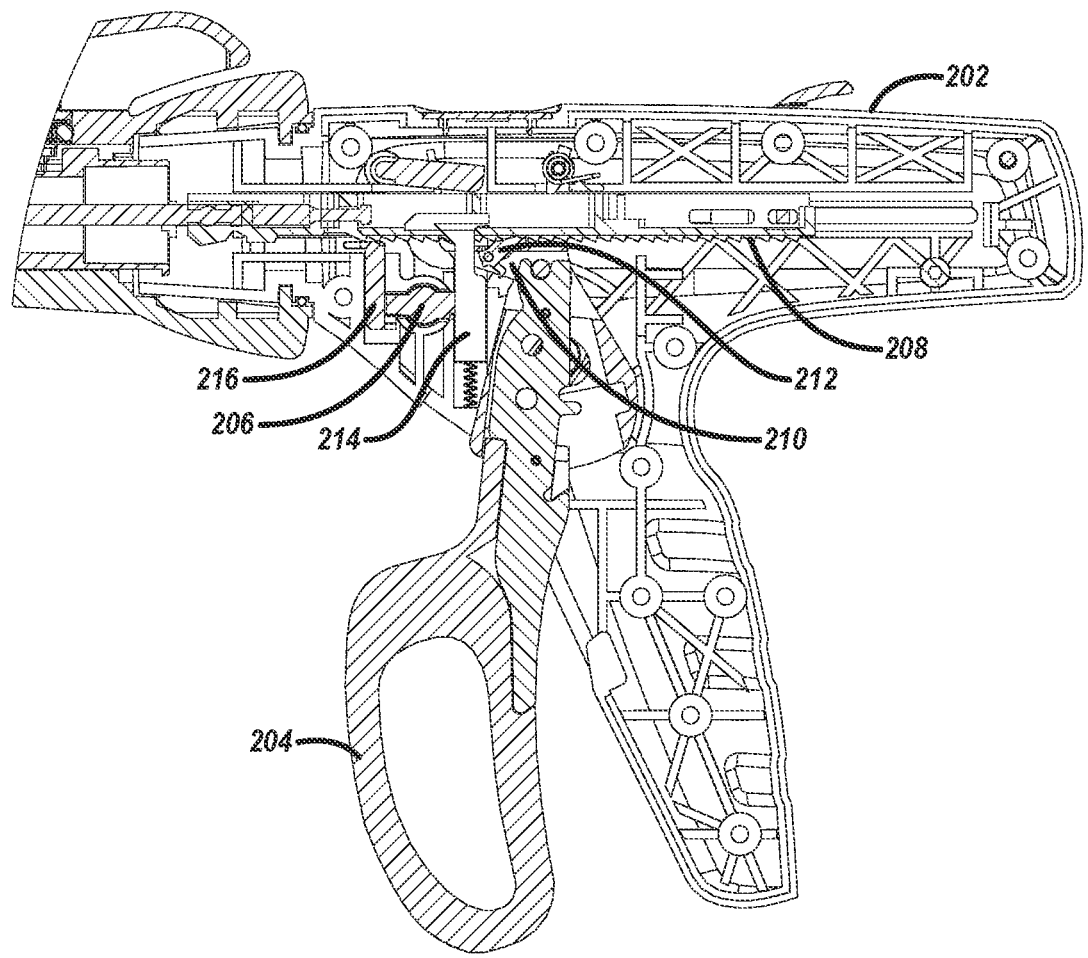
FIG. 2H is a schematic diagram of a surgical handle assembly in a clamped position including a movable handle member, a button, a toothed rack, a driving pawl, a latch, a disengagement mechanism, and a safety latch in accordance with a number of embodiments of the present disclosure.

FIG. 2H is a schematic diagram of a surgical handle assembly 202 in a clamped position including a movable handle member 204, a button 206, a toothed rack 208, a driving pawl 210, a latch 212, a disengagement mechanism 214, and a safety latch 216 in accordance with a number of embodiments of the present disclosure.

The surgical handle assembly 202 can be in a firing mode, as shown in FIG. 2H, able to fire staples when the movable handle member 204 is fully and/or partially actuated by the user and the reloadable cartridge assembly (e.g., reloadable cartridge assembly 103 in FIG. 1) is in a clamped position.

When the surgical handle assembly 202 is firing, the driving pawl 210 can engage the toothed rack 208, the latch 212 cannot engage the toothed rack 208 to advance the toothed rack 208 in a linear proximal direction, and the disengagement mechanism 214 cannot contact the driving pawl 210.

In FIG. 2H, the button 206 is in an unpressed position. In some examples, pressing the button 206 can disengage the safety latch 216. When the button 206 is pressed one of the one or more slanted surfaces (e.g., slanted surfaces 322-1, 322-2 in FIG. 3) of the button 206 can contact one or more surfaces (e.g., slanted surface 326-1, 326-2 in FIG. 3) of the safety latch 216 and cause the safety latch 216 to move in a downward direction. In the lowered position, the safety latch 216 cannot engage the toothed rack 208 to prevent the toothed rack 208 from moving further in the linear distal direction such that staples can be delivered.

The safety latch 216 can prevent a user from accidentally ejecting staples. For example, the safety latch 216 can make the user press the button 206 in order to eject staples. In FIG. 2H, the safety latch 216 cannot engage the toothed rack 208 to prevent the toothed rack 208 from moving in a linear distal direction and staples can be ejected as the user continues to actuate the movable handle member 204 in the proximal direction.

FIG. 3 is a schematic diagram of a safety latch 316, a button 306, and a disengagement mechanism 314 in accordance with a number of embodiments of the present disclosure.

The safety latch 316 can include one or more slanted surfaces 326-1, 326-2, the button 306 can include one or more slanted surfaces 320-1, 320-2, 322-1, 322-2, and the disengagement mechanism 314 can include one or more slanted surfaces 324-1, 324-2.

The one or more slanted surfaces 320-1, 320-2 of the button 306 can contact one or more slanted surfaces 324-1, 324-2 of the disengagement mechanism 314 to activate the disengagement mechanism 314 and move the disengagement mechanism 314 in a downward direction. For example, the slanted surface 320-1 of the button 306 can be a parallel surface to the slanted surface 324-1 of the disengagement mechanism 314 and can contact the slanted surface 324-1 of the disengagement mechanism 314 and/or the slanted surface 320-2 of the button 306 can be a parallel surface to the slanted surface 324-2 of the disengagement mechanism 314 and can contact the slanted surface 324-2 in response to a user pressing the button 306.

The one or more slanted surfaces 322-1, 322-2 of the button 306 can contact one or more slanted surfaces 326-1, 326-2 of the safety latch 316 to move the safety latch 316 in the downward direction. For example, the slanted surface 322-1 of the button 306 can be a parallel surface to the slanted surface 326-1 of the safety latch 316 and can contact the slanted surface 326-1 of the safety latch 316 and/or the slanted surface 322-2 of the button 306 can be a parallel surface to the slanted surface 326-2 of the safety latch 316 and can contact the slanted surface 326-2 of the safety latch 316 in response to a user pressing the button 306.

In some examples, the safety latch 316 can include one or more notches 328-1, 328-2. The one or more notches 328-1, 328-2 can each include one or more slanted surfaces to each create an indentation in the safety latch 316. When the button 306 is pressed towards the ready to fire position, as shown in FIG. 2F, the button 306 is latched inside the 328-1 notch or the 328-2 notch of safety latch 316. For example, if the button 306 is pressed from a first side of the surgical handle assembly (e.g., surgical handle assembly 202 in FIG. 2A-2H), the button 306 will latch with the 328-1 notch and if the button 306 is pressed from a second side of the surgical handle assembly, the button 306 will latch with the 328-2 notch.

The latching of the button 306 with the 328-1 notch or 328-2 notch can create a noise. For example, the noise can be a clicking noise audible to a user. The noise can alert the user that the disengagement mechanism 314 has biased the safety latch 316 in a downward direction to disengage the safety latch 316 from the toothed rack (e.g., toothed rack 208 in FIG. 2A-2H) and the surgical handle assembly (e.g., surgical handle assembly 202 in FIG. 2A-2H) is now in a firing mode.

In some examples, the latching of the button 306 with the 328-1 notch or the 328-2 notch can create a physical cue. For example, the physical cue can be a click that can be felt by a user. The physical cue can alert the user that the disengagement mechanism 314 has biased the safety latch 316 in a downward direction to disengage the safety latch 316 from the toothed rack (e.g., toothed rack 208 in FIG. 2A-2H) and the surgical handle assembly (e.g., surgical handle assembly 202 in FIG. 2A-2H) is now in a firing mode.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A surgical handle assembly apparatus, comprising:
a toothed rack;
a movable handle member;
a driving pawl configured to engage the toothed rack and advance the toothed rack in a linear distal direction in response to the movable handle member advancing in a proximal direction;
a latch configured to engage the toothed rack and advance the toothed rack in a linear proximal direction in response to the movable handle member advancing in a distal direction; and
a disengagement mechanism configured to contact the driving pawl to disengage the driving pawl and the latch from the toothed rack.

2. The apparatus of claim 1, wherein the surgical handle assembly apparatus is configured to be coupled to a reloadable cartridge assembly.

3. The apparatus of claim 2, wherein the reloadable cartridge assembly advances to a clamped position in response to the driving pawl advancing the toothed rack in the linear distal direction.

4. The apparatus of claim 2, wherein the reloadable cartridge assembly advances to an unclamped position in response to the latch advancing the toothed rack in the linear proximal direction.

5. The apparatus of claim 1, wherein the driving pawl and the latch are not in contact with the toothed rack in response to the driving pawl and the latch being disengaged from the toothed rack.

6. The apparatus of claim 1, further comprising a button, wherein the disengagement mechanism is configured to disengage the driving pawl and the latch from the toothed rack in response to the button being pressed.

7. A surgical handle assembly apparatus, comprising:
a toothed rack;
a driving pawl configured to engage the toothed rack and advance the toothed rack in a linear distal direction; and
a disengagement mechanism configured to move downward and contact the driving pawl to disengage the driving pawl from the toothed rack.

8. The apparatus of claim 7, wherein the disengagement mechanism is further configured to disengage a latch from the toothed rack.

9. The apparatus of claim 7, further comprising a button to activate the disengagement mechanism.

10. The apparatus of claim 7, further comprising a movable handle member.

11. The apparatus of claim 10, wherein the toothed rack advances in a linear proximal direction in response to the movable handle member advancing in a distal direction.

12. The apparatus of claim 10, wherein the surgical handle assembly apparatus ejects one or more staples in response to disengaging a safety latch and the movable handle member advancing in a proximal direction.

13. A surgical handle assembly apparatus, comprising:
a toothed rack;
a movable handle member;
a driving pawl configured to engage the toothed rack and advance the toothed rack in a linear distal direction in response to the movable handle member advancing in a proximal direction;
a latch configured to engage the toothed rack and advance the toothed rack in a linear proximal direction in response to the movable handle member advancing in a distal direction;
a button configured to activate a disengagement mechanism that moves downward to contact the driving pawl and disengage the driving pawl and the latch from the toothed rack.

14. The apparatus of claim 13, wherein the surgical handle assembly apparatus is configured to be coupled to a reloadable cartridge assembly.

15. The apparatus of claim 14, wherein the reloadable cartridge assembly ejects one or more staples in response to activating the disengagement mechanism and advancing the movable handle member in the proximal direction.

16. The apparatus of claim 15, wherein the toothed rack moves in a linear distal direction.

17. The apparatus of claim 14, wherein the reloadable cartridge assembly moves to an unclamped position in response to advancing the movable handle member in the distal direction.

18. The apparatus of claim 17, wherein the toothed rack moves in the linear proximal direction.

19. The apparatus of claim 13, wherein the driving pawl and the latch are coupled via a pin.

20. The apparatus of claim 13, wherein the button includes one or more slanted surfaces to contact one or more slanted surfaces of the disengagement mechanism to activate the disengagement mechanism.

* * * * *